United States Patent
Wang et al.

(10) Patent No.: US 7,014,981 B2
(45) Date of Patent: *Mar. 21, 2006

(54) BENZOINDOLE STYRYL COMPOUNDS AND THEIR USES IN HIGH-DENSITY RECORDING MEDIA

(75) Inventors: Shin-Shin Wang, Hsinchu Hsien (TW); Wen-Yih Liao, Hsinchu Hsien (TW); Chii-Chang Lai, Hsinchu Hsien (TW); Chien-Liang Huang, Hsinchu Hsien (TW); Hui-Ping Tsai, Hsinchu Hsien (TW); Chuen-Fuw Yan, Hsinchu Hsien (TW); Jong-Lieh Yang, Hsinchu Hsien (TW); Tzuan-Ren Jeng, Hsinchu Hsien (TW); Ming-Chia Lee, Hsinchu Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 219 days.

This patent is subject to a terminal disclaimer.

(21) Appl. No.: 10/242,755

(22) Filed: Sep. 13, 2002

(65) Prior Publication Data

US 2003/0202458 A1 Oct. 30, 2003

(30) Foreign Application Priority Data

Apr. 19, 2002 (TW) ............................. 91108159 A

(51) Int. Cl.
*G11R 7/27* (2006.01)
*C07D 209/56* (2006.01)
(52) U.S. Cl. ............... 430/270.19; 430/270.18; 430/945; 428/64.8; 369/288; 540/427; 540/490; 540/469

(58) Field of Classification Search ................ 430/270.18–270.21, 560, 945; 428/64.8; 369/288; 548/427, 490, 469
See application file for complete search history.

(56) References Cited

U.S. PATENT DOCUMENTS

| | | | | |
|---|---|---|---|---|
| 5,268,486 A | * | 12/1993 | Waggoner et al. | 548/427 |
| 6,506,539 B1 | * | 1/2003 | Morishima et al. | 430/270.19 |
| 6,589,706 B1 | * | 7/2003 | Liao et al. | 430/270.1 |
| 6,815,031 B1 | * | 11/2004 | Huang et al. | 428/64.1 |
| 6,821,708 B1 | * | 11/2004 | Liao et al. | 430/270.19 |

FOREIGN PATENT DOCUMENTS

EP 1130063 * 9/2001

* cited by examiner

*Primary Examiner*—Martin Angebranndt
(74) *Attorney, Agent, or Firm*—Birch, Stewart, Kolasch & Birch, LLP

(57) ABSTRACT

The invention discloses new benzoindole styryl compounds and its use for a high-density optical recording medium. The invention uses the dyes of the new benzoindole styryl compounds to form the recording layer of high-density recording media. The new benzoindole styryl compounds are easy to prepare and purify, so they are cheaper when comparing to the compounds generally used in high-density optical recording media. The benzoindole styryl compounds has a maximum absorption for the light wavelength in the range of 500 nanometers to 700 nanometers. The benzoindole styryl compounds also have high sensitivity and chemical stability for light and heat. Using the new benzoindole styryl compounds to form a high-density optical recording medium can match up with the short-wavelength laser beam for high-density optical recording media and have the advantage of a stable quality.

25 Claims, 3 Drawing Sheets

BENZOINDOLE STYRYL COMPOUNDS AND THEIR USES IN HIGH-DENSITY RECORDING MEDIA

BACKGROUND OF THE INVENTION

1. Field of Invention

The invention relates to new benzoindole styryl compounds and, in particular, to new benzoindole styryl compounds and their uses in high-density optical recording media.

2. Related Art

With the coming of information and multimedia era, computer, communication and consumer electronics have higher demands for larger storage density and capacity. Due to the large amount of information exchange, it is desirable to develop a high-density, small and cheap storage medium. Conventional magnetic storage media are already insufficient for current uses; high-density optical information storage media are the main subject under study. There had been some proposed principles and methods for increasing the storage density in optical information storage media. Some of them are important and have already been successfully implemented. One method is to shorten the wavelength of the laser beam. For example, red lasers are replaced by blue lasers. One can also achieve the same goal by increasing the NA (Numerical Aperture) of the lens. Another method is to improve the digital signal coding means or to utilize optical disk recording with the so-called ultra-high resolution near-field optical structure. These methods can all effectively increase the storage density.

On the other hand, another research field of optical information storage media is to replace the organic dyes used in optical recording layers by those with better optical properties. In recent years, one-time recording compact discs (CD-R) have become people's favorite storage media due to their cheap prices, fast burning speeds, convenience in carriage, and high compatibility among different personal computers. To achieve high-density storage, dyes for such media as one-time recording digital versatile discs (DVD-R) with 4.7 GB capacity have become an important subject under research. Since the laser for high-density storage media such as DVD-R's has a light wavelength of 650 nm, which is different from that of the laser for CD-R's (780 nm), the dyes cannot be shared between the two kinds of media. This is why developing new organic dyes for high-density storage media is an urgent need.

SUMMARY OF THE INVENTION

It is an objective of the invention to provide new benzoindole styryl compounds and their uses in high-density recordable optical discs. Such benzoindole styryl compounds have a maximum absorption for light wavelengths in the range of 500 nanometers to 700 nanometers (λ=500 nm~700 nm). The benzoindole styryl compounds also have high sensitivity, chemical stability toward light and heat and good solubility for organic solutions.

To achieve the above objective, the invention provides new benzoindole styryl compounds which have the following graphical chemical structure (I).

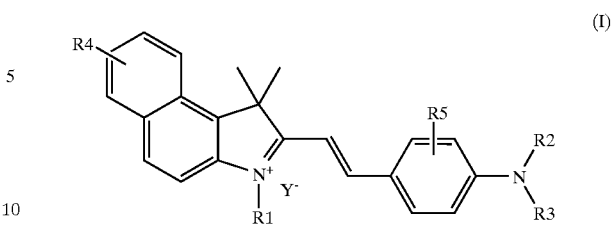

As shown in the structure (I), $R^1$, $R^2$, $R^3$, $R^4$, $R^5$ and $Y^-$ represent groups connected to different positions on the chemical structure. In particular, when $R^1$ is $CH_2C_6H_4CO_2R^6$, $(CH_2)_nSO_3R^7$, or $(CH_2)_nCO_2R^7$, $Y^-$ can be selected from $(TCNQ^-)_n$ (teteacyano-p-quinodimethane) and $(TCNE^-)_n$, (tetracyanoetylene) (n=0, 1), $ClO_4^-$, $SbF_6^-$, $PF_6^-$, $BF_4^-$ and halide ions ($X^-$). $R^2$ and $R^3$ are same or different groups selected from hydrogen atoms, alkyl groups with one to eight carbons ($C_{1-8}$), alkyl-oxygen groups with one to eight carbons ($C_{1-8}$) and alkyl-ester groups one to eight carbons ($—CO_2R^8$). $R^2$ and $R^3$ can be connected to form a pyrrolidine ring, $R^2$ and $R^3$ can be connected to benzene ring to form a julolidine ring. $R^4$ and $R^5$ are same or different groups selected from hydrogen atoms, alkyl groups with one to eight carbons ($C_{1-8}$), trifluoromethyl groups, alkyl-oxygen group, carboxyl groups, nitric groups, amide groups ($CONR^9R^{10}$), sulfonic groups, $SO_3R^{11}$, alkyl-ester groups with one to eight carbons ($C_{1-8}$), and halide ions ($X^-$).

When the choice of $Y^-$ needs to match $R^1$ and $R^1$ is an alkyl group with one to eight carbons ($C_{1-8}$), $Y^-$ must be one of $(TCNQ^-)_n$, (teteacyano-p-quinodimethane) and $(TCNE^-)_n$, (tetracyanoetylene)(n=0, 1). Moreover, when $R^1$ is one of $CH_2C_6H_4CO_2R^6$, $(CH_2)_nSO_3R^7$, and $(CH_2)_nCO_2R^7$, $Y^-$ can be one of $(TCNQ^-)_n$, (teteacyano-p-quinodimethane), $(TCNE^-)_n$, (tetracyanoethylene) (n=0, 1), $ClO_4^-$, $SbF_6^-$, $PF_6^-$, $BF_4$ and halide ions.

When $R_1$ of the new benzoindole styryl compound is one of $(CH_2)_nCO_2R^6$, $(CH_2)_nSO_3R^7$, and $(CH_2)_nCO_2R^7$, $R^6$ and $R^7$ can be an alkyl or alkyl fluoride ($C_2F_4$, $CF_3$) with one to eight carbons.

When $R^4$ and $R^5$ in the new benzoindole styryl compound is an alkyl-ester group ($—CO_2R^8$) with one to eight carbons ($C_{1-8}$), $R^8$ can be an alkyl or alkyl fluoride ($C_2F_4$, $CF_3$) with one to eight carbons. If $R^4$ and $R^5$ are amide groups ($—CONR^9R^{10}$), $R^9$ and $R^{10}$ may be same or different groups. $R^9$ and $R^{10}$ can be hydrogen atoms or alkyl groups with one to six carbons. When $R^4$ and $R^5$ are $—SO_3R^{11}$ groups, $R^{11}$ may be hydrogen atoms or alkyl groups with one to six carbons. The above choices of groups can be selectively applied to the chemical formula (I).

Furthermore, the manufacturing method of the new benzoindole styryl compounds requires the reaction between the compound (II) and the compound (III) in an organic solution. The manufacturing method of the new benzoindole styryl compounds is explicitly as follows:

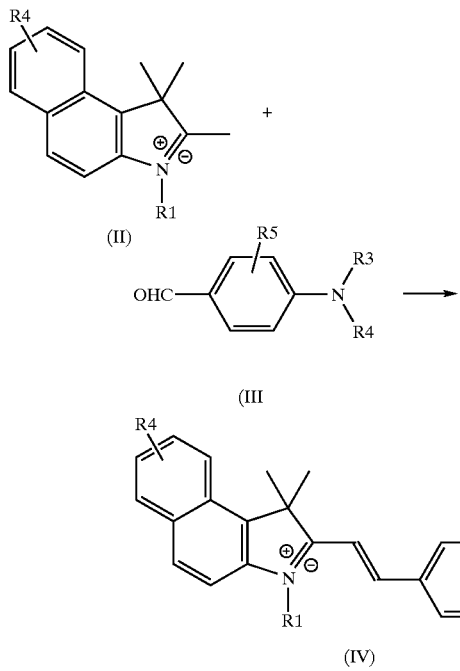

(II)

(III)

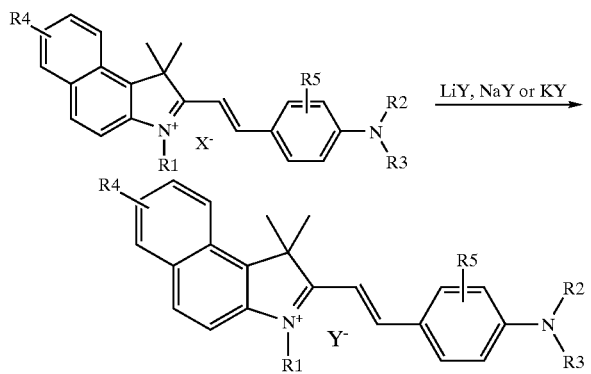

(IV)

Mix the compound (II) and the compound (III) in an organic solution. They undergo a reaction to obtain a benzoindole styryl compound (IV) with halide ions (X⁻).

Finally, as shown in the following reaction formula, the benzoindole styryl compound (IV) with halide ions and one of the lithium, sodium and potassium salt (LiY, NaY, KY) are mixed in an organic solution to exchange ions, obtaining a new chemical compound with the chemical formula $(I)_{(I)}$ The disclosed benzoindole styryl compounds can be directly applied to usual DVD's and the recording layers of other high-density data storage media.

It is another objective of the invention to provide a high-density data storage medium using the new benzoindole styryl compound dyes in its recording layer. Since this kind of benzoindole styryl compounds is easy to synthesize and purify, they are cheaper than other usual dyes. In addition, the high-density data storage media using the disclosed benzoindole styryl compounds have good photosensitivity and superior chemical stability in the recording layer.

It is yet another objective of the invention to use the new benzoindole styryl compounds as the recording layer of a recordable optical disc to form a high-density optical recording medium. The recordable optical disc comprises: a first substrate, which is a transparent substrate with grooves, a recording layer, which is formed on the first substrate surface using the new benzoindole styryl compounds, a reflective layer formed on the recording layer, a second substrate, which is a transparent substrate with grooves connected to the reflective layer with an attachment layer. One feature of the invention is that the new benzoindole styryl compounds are used as dyes in the recording layer.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

This specification discloses new benzoindole styryl compounds and their uses in high-density recordable optical discs. The benzoindole styryl compounds have the structure in the chemical formula (I) with different group combinations.

Figure 1:
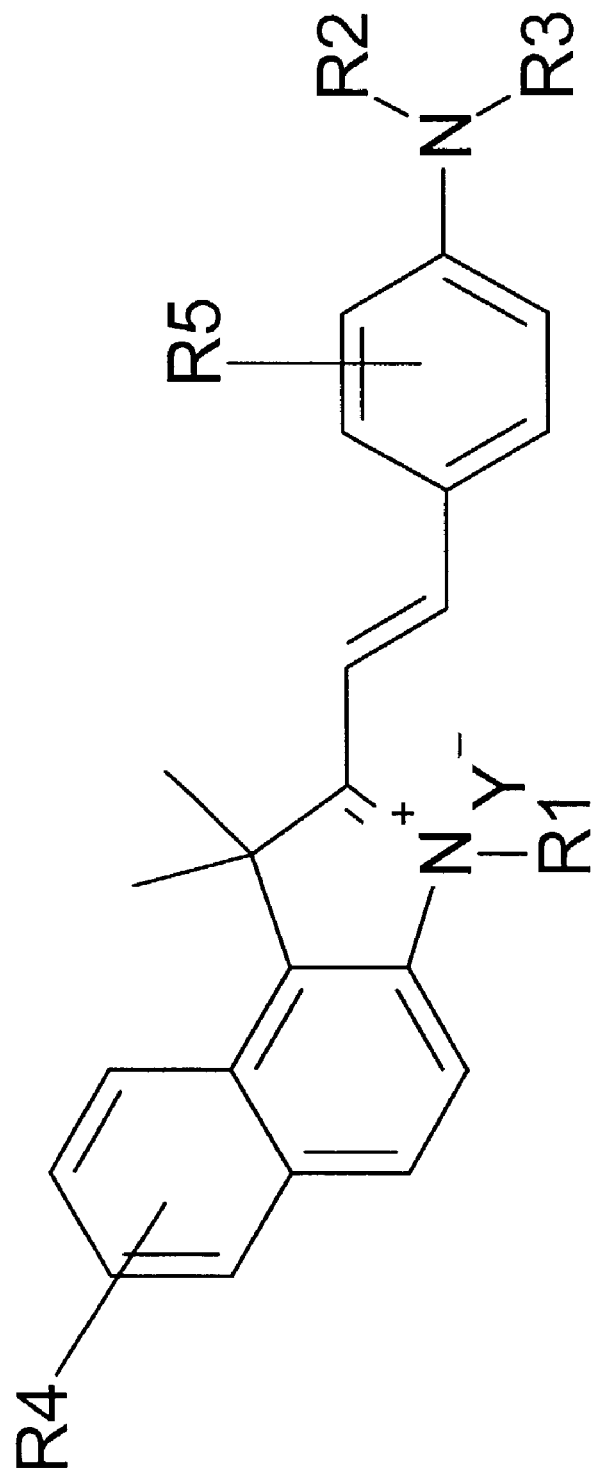
FIG. 1 is a schematic view of the chemical formula (I) of the disclosed benzoindole styryl compounds.

To explain the invention, we illustrate in the following paragraphs the synthesis procedure and the chemical formula of the new benzoindole styryl compounds. FIG. 1 shows the general chemical structure of the benzoindole styryl compounds.

In a first embodiment, 5 g of initial material (II) with an $R_1$ being —$CH_2C_6H_4CO_2CH_3$ and 2.1 g of material (III) with the same $R_2$ and $R_3$ (—$C_2H_5$) are dissolved in 120 ml alcohol. The system is heated for three to four hours of reaction. After the reaction is completed, the system is filtered and dried to obtain a green solid crystal (A) with a chemical formula (IV), where $R^4$ and $R^5$ are hydrogen atoms (H), X⁻ is an iodine ion, and the reaction yield is 90%. After material analysis, we find that the compound (A) has an absorption wavelength of 583 nm ($UV_{max}$=583 nm). The compound (A) further undergoes an ion exchange reaction with one of the lithium, sodium and potassium ionic compounds in an organic solution, forming various kinds of new compounds with the chemical formula (I). The following lists the manufacturing procedure and properties of the new compounds (A) formed from the ion exchange reaction:

(1) Take 3.2 g of the solid crystal of compound (A) and 0.73 g of $NaClO_4$ and dissolve them in 50 ml alcohol. Heat them up to perform ion exchanges. After the reaction, the products are filtered and dried to obtain dark green solid crystal of compound (B) with the chemical formula (I), $R^4$ and $R^5$=H, and Y=$ClO_4^-$. The reaction yield is computed to be 95%. The material analysis indicates that the compound (B) has an absorption wavelength of 582.5 nm ($UV_{max}$=582.5 nm) and the absorption coefficient $\epsilon$=7.36× $10^4$.

(2) Take 3.2 g of the solid crystal of compound (A) and 1 g of $NaPF_6$ and dissolve them in 50 ml alcohol. Heat them up to perform ion exchanges. After the reaction, the products are filtered and dried to obtain gold green solid crystal of compound (C) with the chemical formula (I), $R^4$ and $R^5$=H, and Y=$PF_6^-$. The reaction yield is computed to be 96%. The material analysis indicates that the compound (C) has an absorption wavelength of 583 nm ($UV_{max}$=583 nm).

(3) Take 3.2 g of the solid crystal of compound (A) and 1.6 g of $NaSbF_6$ and dissolve them in 50 ml alcohol. Heat them up to perform ion exchanges. After the reaction, the products are filtered and dried to obtain green thin needle crystals (D) with the chemical formula (I), $R^4$ and $R^5$=H, and Y=$SbF_6^-$. The reaction yield is computed to be 95%. The material analysis indicates that the compound (D) has an absorption wavelength of 583.5 nm ($UV_{max}$=583.5 nm) and the absorption coefficient $\epsilon$=8.62×10$^4$.

(4) Take 3.2 g of the solid crystal of compound (A) and 1.27 g of LiTCNQ and dissolve them in 50 ml alcohol. Heat them up to perform ion exchanges. After the reaction, the products are filtered and dried to obtain dark brown crystals (E) with the chemical formula (I), $R^4$ and $R^5$=H, and Y=$TCNQ^-$. The reaction yield is computed to be 94%. The material analysis indicates that the compound (E) has a breaking temperature of 233° C., an absorption wavelength of 583 nm ($UV_{max}$=583 nm) and an absorption coefficient $\epsilon$=7.38×10$^4$.

A second embodiment of the invention also has new compounds with the chemical formula (I). The side group $R^1$ is selected to be —$(CH_2)_4CO_2CH_3$. Take 4.39 g compound with the chemical formula (II) as the initial material, where $R^1$ is —$(CH_2)_4CO_2CH_3$, and 2.1 g compound with the chemical formula (III), where $R^2$ and $R^3$ are the same —$C_2H_5$ groups, and dissolve them into 100 ml alcohol. Heat up the alcohol to its backflow temperature for reaction for three to four hours. After the reaction is completed, the products are filtered and dried to obtain green solid crystals of the compound (F), with a chemical formula (IV), $R^4$ and $R^5$=H, X=$I^-$, and a reaction yield of 90%. The material analysis indicates that the compound (F) has an absorption wavelength of 572 nm ($UV_{max}$=572 nm). The compound (F) and different lithium, sodium, and potassium ionic compounds are mixed in an organic solution for ion exchanges, forming various kinds of new compounds with the chemical formula (I). The following lists the manufacturing procedure and properties of the new compounds (F) formed from the ion exchange reaction:

(5) Take 3 g of the solid crystal of compound (F) and 0.74 g of $NaClO_4$ and dissolve them in 50 ml alcohol. Heat them up to perform ion exchanges. After the reaction, the products are filtered and dried to obtain dark green solid crystals of compound (G) with the chemical formula (I), $R^4$ and $R^5$=H, and Y=$ClO_4^-$. The reaction yield is computed to be 95%. The material analysis indicates that the compound (G) has an absorption wavelength of 573 nm ($UV_{max}$=573 nm).

(6) Take 3 g of the solid crystal of compound (F) and 1 g of $NaPF_6$ and dissolve them in 50 ml alcohol. Heat them up to perform ion exchanges. After the reaction, the products are filtered and dried to obtain golden green solid crystals of compound (H) with the chemical formula (I), $R^4$ and $R^5$=H, and Y=$PF_6^-$. The reaction yield is computed to be 95%. The material analysis indicates that the compound (H) has an absorption wavelength of 573 nm ($UV_{max}$=573 nm).

(7) Take 3 g of the solid crystal of compound (F) and 1.6 g of $NaSbF_6$ and dissolve them in 50 ml alcohol. Heat them up to perform ion exchanges. After the reaction, the products are filtered and dried to obtain blue needle crystals of compound (I) with the chemical formula (I), $R^4$ and $R^5$=H, and Y=$SbF_6^-$. The reaction yield is computed to be 95%. The material analysis indicates that the compound (I) has a breaking temperature of 266° C., an absorption wavelength of 573 nm ($UV_{max}$=573 nm), and an absorption coefficient $\epsilon$=8.6×10$^4$.

(8) Take 3 g of the solid crystal of compound (F) and 1.27 g of LiTCNQ and dissolve them in 50 ml alcohol. Heat them up to perform ion exchanges. After the reaction, the products are filtered and dried to obtain dark brown solid crystals of compound (J) with the chemical formula (I), $R^4$ and $R^5$=H, and Y=$TCNQ^-$. The reaction yield is computed to be 94%. The material analysis indicates that the compound (J) has a breaking temperature of 230° C., an absorption wavelength of 573 nm ($UV_{max}$=573 nm), and an absorption coefficient $\epsilon$=9.5×10$^4$.

The compounds (A) and (F) formed in the first and second embodiments are benzoindole styryl compounds with iodine ions. They are mixed with lithium, sodium and potassium salts in an organic solution for ion exchanges. After the reaction is completed, the products are filtered and dried to obtain the disclosed benzoindole styryl compounds (B), (C), (D), (E), (G), (H), (I), (J), (K) and (L). The chemical formulas and the maximal absorption wavelengths of the various new compounds are listed in Table 1.

TABLE 1

The chemical formulas and the maximal absorption wavelengths of various new compounds.

| No | Compound structure | λmax (nm) | ε |
|---|---|---|---|
| A | 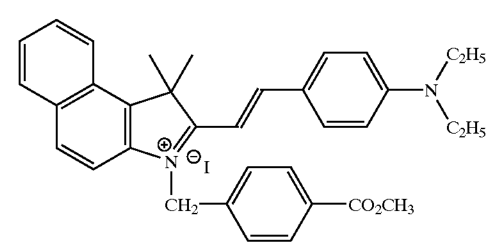 | 583 | — |

TABLE 1-continued

The chemical formulas and the maximal absorption wavelengths of various new compounds.

| No | Compound structure | λmax (nm) | ε |
|---|---|---|---|
| B | (structure with ClO₄⁻, CH₂-C₆H₄-CO₂CH₃) | 582.5 | 7.36 × 10⁴ |
| C | (structure with PF₆⁻, CH₂-C₆H₄-CO₂CH₃) | 583 | — |
| D | (structure with SbF₆⁻, CH₂-C₆H₄-CO₂CH₂CF₃CF₂CF₂H) | 584 | 1.09 × 10⁵ |
| E | (structure with TCNQ⁻, CH₂-C₆H₄-CO₂CH₃) | 583 | 7.38 × 10⁴ |
| F | (structure with I⁻, CH₂-(CH₂)₃-CO₂CH₃) | 572 | — |
| G | (structure with ClO₄⁻, CH₂-(CH₂)₃-CO₂CH₃) | 573 | — |

TABLE 1-continued

The chemical formulas and the maximal absorption wavelengths of various new compounds.

| No | Compound structure | λmax (nm) | ε |
|---|---|---|---|
| H | 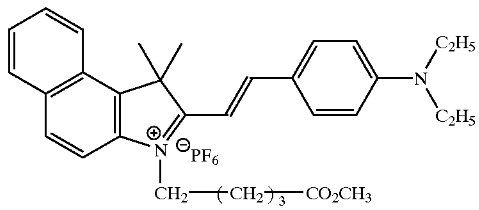 | 573 | — |
| I | 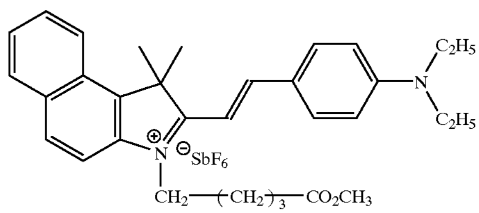 | 573 | $8.76 \times 10^4$ |
| J | 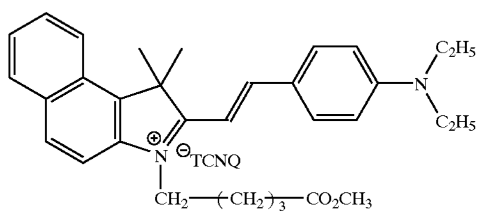 | 573 | $9.5 \times 10^4$ |
| K | 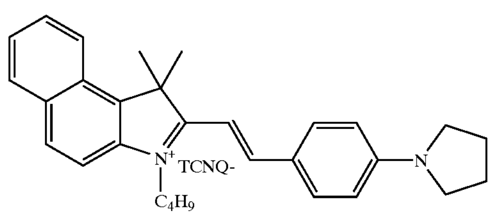 | 572.5 | $8.37 \times 10^4$ |
| L | 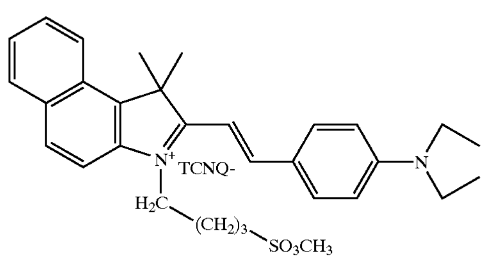 | 573 | — |
| M | 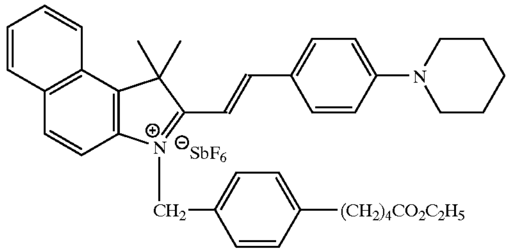 | 583.5 | $9.53 \times 10^4$ |

TABLE 1-continued

The chemical formulas and the maximal absorption wavelengths of various new compounds.

| No | Compound structure | λmax (nm) | ε |
|----|-------------------|-----------|---|
|    | 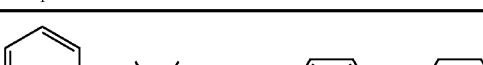 | 583.5 | $1.12 \times 10^5$ |

After the new benzoindole styryl compounds obtained from the disclosed embodiments are appropriately diluted and processed, we then obtain dyes for high-density optical discs. One can also mix more than one kinds of benzoindole styryl compounds or other dyes in order to obtain required properties for high-density optical discs.

Figure 2:
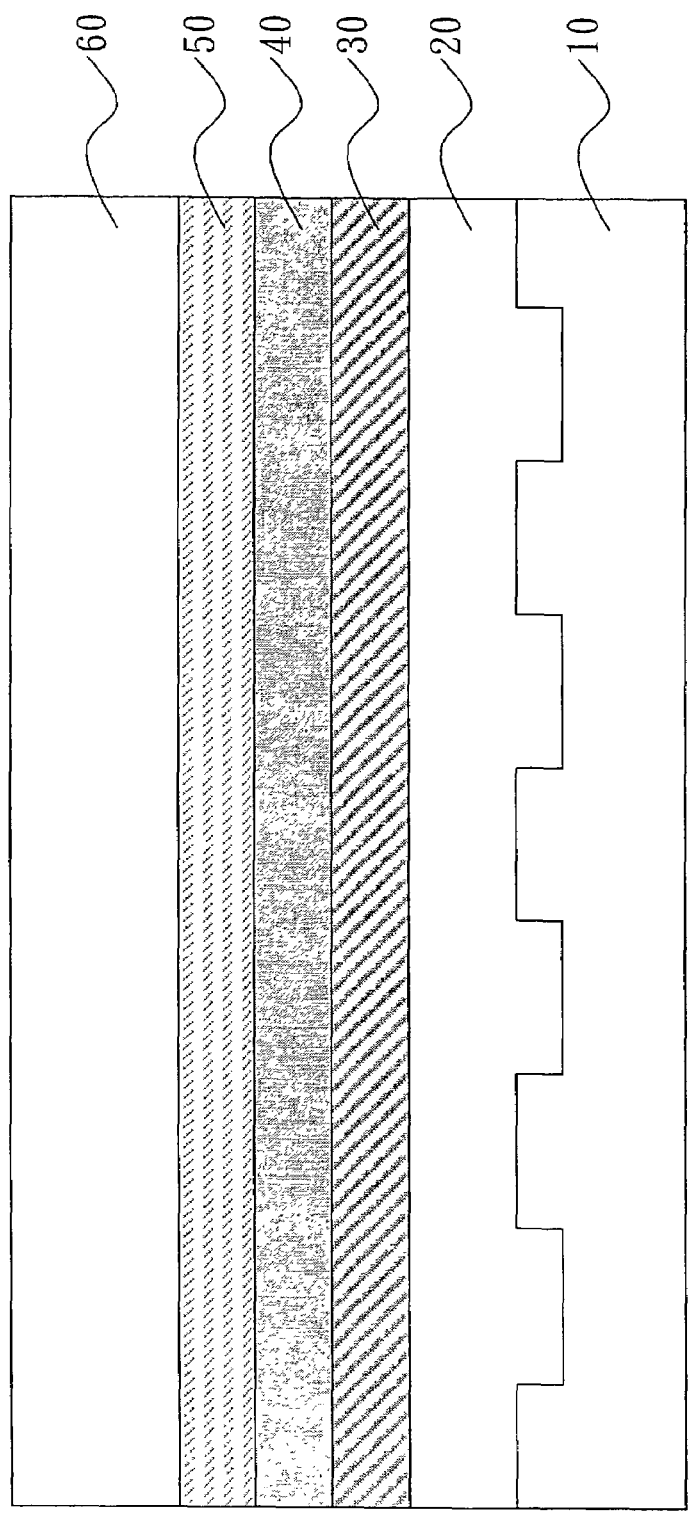
FIG. 2 is a schematic view of an embodiment of the invention using the new benzoindole styryl compound dyes in high-density recordable optical discs.

We further apply the new benzoindole styryl compounds to form the recording layer of high-density recordable optical discs. With reference to FIG. 2, the high-density recordable optical disc is comprised of: a first substrate 10, which is a transparent substrate, a recording layer 20, which is benzoindole styryl compounds formed on the surface of the first substrate 10, and a reflective layer 30, which is formed on the recording layer 20 and coated with a resin protection layer 40, a second substrate 60, which is a transparent substrate, and an attachment layer, which connects the resin protection layer 40 and the second substrate 60.

The benzoindole styryl compounds mentioned here has the structure shown in the chemical formula (I) and can be combined with different ion groups. The material selection and manufacturing method of the benzoindole styryl compound dyes can be understood from the following text.

The steps of the manufacturing method are as follows: First, dissolve 1.8 g of the new benzoindole styryl compounds in 2,2,3,3-tetrafluoropropanol and make a 100 g solution. This solution is applied on the first substrate 10 by coating. Afterwards, a drying procedure is employed to form a recording layer 20 of the new benzoindole styryl compounds on the substrate surface. The recording layer 20 is formed with a reflective layer 30 by sputtering a metal material, followed by the application of a resin protection layer 40. Finally, a second substrate is provided to combine with the resin protection layer 40 using an attachment layer. This completes the manufacturing of a high-density recordable optical disc.

The first substrate and the second substrate are transparent substrates with lands and grooves. The track pitch is between 0.3 μm and 0.8 μm. The groove depth is between 70 nm and 200 nm. The material of the substrate can be polyesters, polycarbonates (PC), PMMA, MCOC, etc.

The formation method of the recording layer can be spin coating, vacuum evaporation, jet coating, rolling coating, or soaking. It is preferably to use spin coating, forming a recording layer of 70 nm to 250 nm thick.

The organic solution for coating can be selected from alcohols with one to six carbons ($C_{1-6}$), ketones with one to six carbons, ethers with one to six carbons, halide compounds, cyclanes and amides. The alcohols can be methanol, ethanol, isopropanol, diacetonalchol (DAA), 2,2,3,3-tetrafluoropropanol, trichloroethanol, 2-chloroethanol, octafluoropentanol, or hexafluorobutanol. The ketones can be acetone, methyl isobutyl ketone (MIBK), methyl ethyl ketone (MEK), and 3-hydroxy-3-methyl-2-butanone. The suitable halide compounds include chloroform, dichloromethane, and 1-chlorobutane. The amides include dimethylformamide (DMF) and dimethylacetamide (DMA). The cyclane is methylcyclohexane (MCH).

The material of the reflective layer sputtered on the recording layer is selected from gold, silver, aluminum, silicon, copper, silver-titanium alloys, silver-chromium alloys, and silver-copper alloys. The combination of the first substrate and the second substrate can be achieved using spin coating, half-tone printing, hot gluing, and double-sided tapes.

Figure 3:
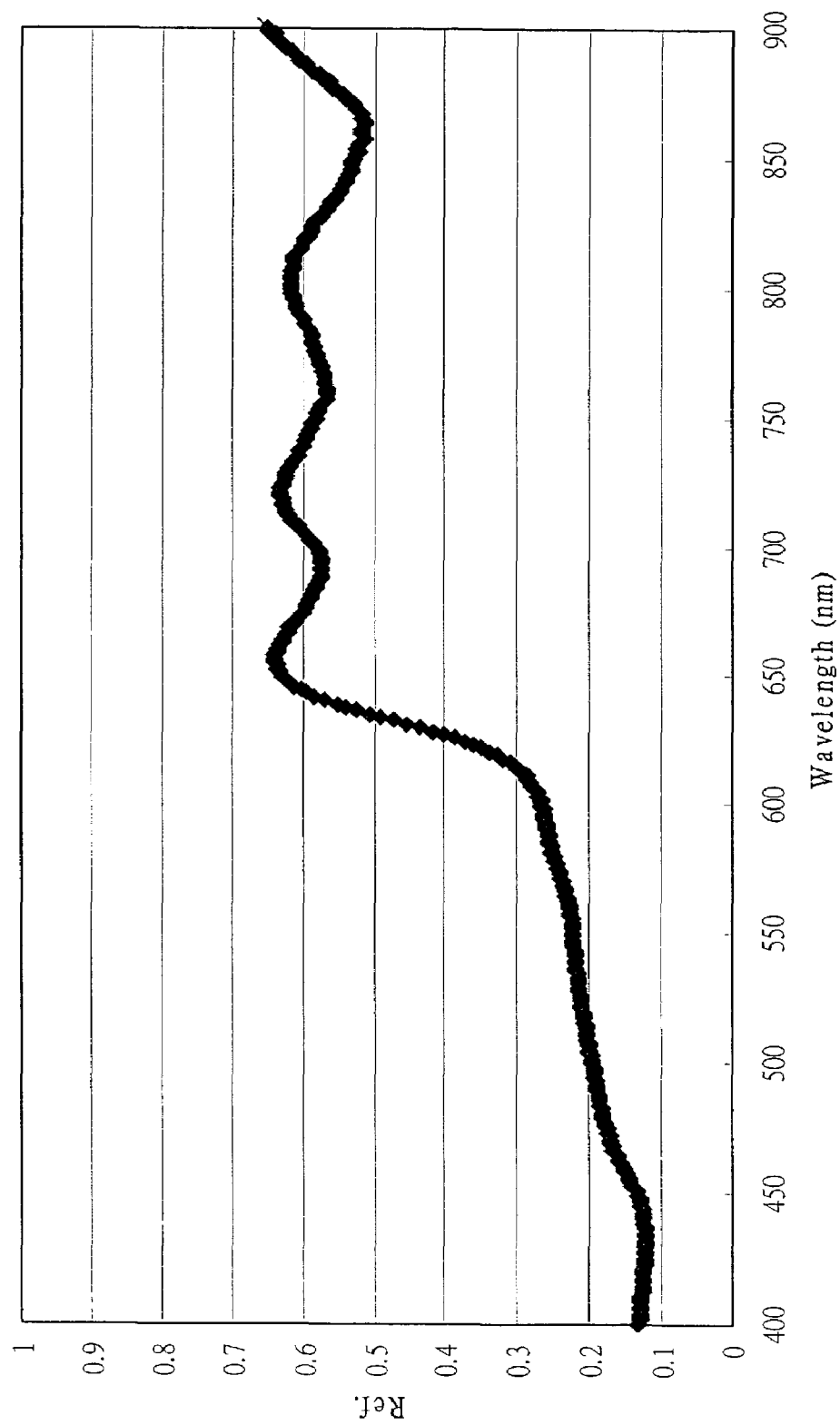
FIG. 3 shows the spectrum of the reflective index versus the wavelength for the disclosed high-density recordable optical discs.

The thickness of the recording layer on the substrate in this embodiment is between 70 nm and 250 nm. A reflective layer of 50 nm to 200 nm thick is directly coated on the recording layer. Finally, the substrate formed with the reflective layer and the recording layer is combined with another blank substrate with a thickness of 0.6 mm. (As described before, the connection can be achieved using spin coating, half-tone printing, hot gluing, and double-sided tapes.) A high-density recordable optical disc of 120 mm thick can be thus formed. FIG. 3 shows the optical spectrum of the reflective index of the high-density recordable optical disc versus the wavelength in accordance with the invention. As shown in the drawing, the reflective index is greater than 45% for wavelength between 635 nm and 650 nm.

We further use in the embodiment a PULSTEC DDU-1000 evaluation test machine to write and read the test results.

The recording conditions are: the constant linear velocity (CLV) is 3.5 m/s, the wavelength is 658 nm, the numerical aperture (NA) is 0.6, and the writing power is 7~14 mW. The reading conditions are: the CLV is 2.5 m/s, the wavelength is 658 nm, the NA is 0.6, and the reading power is 0.5~1.5 mW. Table 2 has the CNR values under different writing powers in the embodiment.

TABLE 2

| Writing Power (mW) | 7 | 8 | 9 | 10 | 11 | 12 | 13 | 14 |
|---|---|---|---|---|---|---|---|---|
| 3T CNR (dB) | 50.9 | 56.6 | 58.3 | 58.4 | 58.7 | 59.1 | 58.8 | 58.3 |

From Table 2, we see that when the writing power is above 8 mW, the CNR value is greater than 55 dB. CNR even reaches 58 dB and the jitter is 12.7% when the writing power is above 9 mW. This means that the high-density optical disk according to the invention has the advantages of high sensitivity and chemical stability of light and heat.

EFFECTS OF THE INVENTION

The disclosed new benzoindole styryl compounds are easy to synthesize and purify. Therefore, they are much cheaper than normal dye compounds used in DVD optical discs. The R1 side group in the structure of new benzoindole styryl compounds can enhance its photosensitivity and stability to light and heat. These benzoindole styryl compounds have extremely good solubility in organic solutions, which is ideal for the spin coating procedure for the optical discs. Thus, it is of great advantage to use the new benzoindole styryl compounds in the recording layer of high-density recordable optical discs. The disclosed recordable optical discs in comparison with conventional one made of normal dye compounds will be cheaper in price, while having better stability under the shorter laser beam used for high-density recordable media.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A benzoindole styryl compound, which has the following chemical structure:

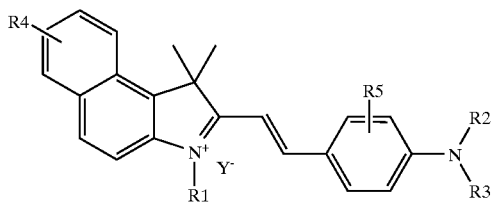

(I)

where $R^1$ is $CH_2C_6H_4CO_2R^6$, $R^6$ being an alkyl or fluorinated alkyl group;

$R^2$ and $R^3$ are selected from the group consisting of hydrogen atoms, alkyl groups containing one to eight carbons ($C_{1-8}$), alkyl-oxygen groups containing one to eight carbons, alkyl-ester groups (—$CO_2R^8$) containing one to eight carbons, and a pyrrolidine ring formed by connecting $R^2$ and $R^3$, a julolidine ring formed by one of $R^2$ and $R^3$ to benzene ring, $R^8$ being an aklyl or fluorinated alkyl group;

$R^4$ and $R^5$ are selected the group consisting of hydrogen atoms, alkyl groups with one to eight carbons ($C_{1-8}$), trifluoromethyl groups, alkyl-oxygen group, carboxyl groups, nitric groups, amide groups (CONR$^9$R$^{10}$), sulfonic groups, SO$_3$R$^{11}$, alkyl-ester groups with one to eight carbons ($C_{1-8}$), and halide ions (Y$^-$, each of R$^9$, R10 and R$^{11}$ being hydrogen or an aklyl group;

wherein the choice of Y$^-$ needs to match R$^1$ and Y$^-$ is selected from the group consisting of (TCNQ$^-$)$_n$ (tetracyano-p-quinodimethane), (TCNE$^-$)$_n$ (tetracyanoethylene)

(n=0, 1), ClO$_4$—, SbF$_6$—, PF$_6$—, BF$_4$ and halide ions.

2. The benzoindole styryl compound of claim 1, wherein $R^6$ is selected from the group consisting of alkyl groups containing one to eight carbons, $C_2F_4$, $CF_3$ and fluorinated alkyl groups.

3. The benzoindole styryl compound of claim 1, wherein $R^4$ and $R^5$ are alkyl-ester groups ($CO_2R^8$) containing one to eight carbons, $R^8$ is selected from the group consisting of an alkyl groups, $C_2F_4$, and $CF_3$.

4. The benzoindole styryl compound of claim 1, wherein when $R^4$ and $R^5$ are amide groups (—CONR$^9$R$^{10}$), $R^9$ and $R^{10}$ are selected from the group consisting of hydrogen atoms and alkyl groups containing one to six carbons.

5. The benzoindole styryl compound of claim 1, wherein when $R^4$ and $R^5$ are —SO$_3$R$^{11}$ groups and R$^{11}$ is selected from the group consisting of hydrogen atoms and alkyl groups containing one to six carbons.

6. A high-density recordable optical disc, which comprises:

a first substrate, which is a transparent substrate;
a recording layer, which has an imine salt formed on one surface of the first substrate;
wherein the imine salt has the following chemical structure:

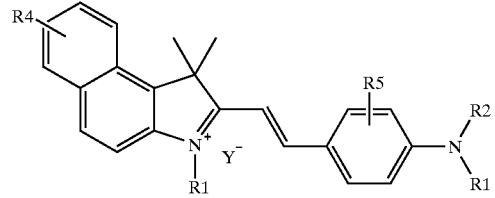

where $R^1$ is $CH_2C_6H_4CO_2R^7$, $R^7$ being an alkyl or fluorinated alkyl group;

$R^2$ and $R^3$ are selected from the group consisting of hydrogen atoms, alkyl groups containing one to eight carbons ($C_{1-8}$), alkyl-oxygen groups containing one to eight carbons, alkyl-ester groups (—$CO_2R^8$) containing one to eight carbons, and a a pyrrolidine ring formed by connecting $R^2$ and $R^3$, a julolidine ring formed by one of $R^2$ and $R^3$ to benzene ring, $R^8$ being an alkyl or fluorinated alkyl group;

$R^4$ and $R^5$ are selected the group consisting of hydrogen atoms, alkyl groups with one to eight carbons ($C_{1-8}$), trifluoromethyl groups, alkyl-oxygen group, carboxyl groups, nitric groups, amide groups (CONR$^9$R$^{10}$), sulfonic groups, SO$_3$R$^{11}$, alkyl-ester groups with one to eight carbons ($C_{1-8}$), and halide ions (Y$^-$), each of R$^9$, R$^{10}$ and R$^{11}$ being hydrogen or an alkyl group;

wherein the choice of Y$^-$ needs to match R$^1$ and Y$^-$ is selected from the group consisting of (TCNQ$^-$)$_n$ (tetracyano-p-quinodimethane), (TCNE$^-$)$_n$ (tetracyanoethylene)

(n=0, 1), ClO$_4$—, SbF$_6$—, PF$_6$—, BF$_4$ and halide ions;

a reflective layer, which is provided on the recording layer;

a second substrate, which is a transparent substrate; and an attachment layer, which is used to connected the reflective layer and the second substrate.

7. The imine salt of claim 6, wherein $R^7$ is selected from the group consisting of alkyl groups ($CO_2R^8$) containing one to eight carbons, $C_2F_4$, $CF_3$ and fluorinated alkyl groups.

8. The high-density recordable optical disc of claim 6, wherein $R^4$ and $R^5$ are alkyl-ester groups ($CO_2R^8$) containing one to eight carbons, $R^8$ is selected from the group consisting of an alkyl groups, $C_2F_4$, and $CF_3$.

9. The high-density recordable optical disc of claim 6, wherein when $R^4$ and $R^5$ are amide groups ($-CONR^9R^{10}$), $R^9$ and $R^{10}$ are selected from the group consisting of hydrogen atoms and alkyl groups containing one to six carbons.

10. The high-density recordable optical disc of claim 6, wherein when $R^4$ and $R^5$ are $-SO_3R^{11}$ groups and $R^{11}$ is selected from the group consisting of hydrogen atoms and alkyl groups containing one to six carbons.

11. The high-density recordable optical disc of claim 6, wherein each of the first substrate and the second substrate is a transparent substrate having lands and grooves with a track pitch preferably between 0.3 μm to 0.8 μm and a groove depth between 70 nm and 200 nm.

12. The high-density recordable optical disc of claim 6, wherein the first substrate and the second substrate are made of a material selected from the group consisting of polyesters, polycarbonates (PC), PMMA and MCOC.

13. The high-density recordable optical disc of claim 6, wherein the recording layer is formed using a method selected from spin coating, vacuum evaporation, jet coating, rolling coating, and soaking.

14. The high-density recordable optical disc of claim 6, wherein the thickness of the recording layer is between 70 nm and 250 nm.

15. The high-density recordable optical disc of claim 6, wherein the new benzoindole styryl compounds is first dissolved in an organic solution and then applied on the surface of the first substrate by spin coating to form the recording layer.

16. The high-density recordable optical disc of claim 15, wherein the organic solution is selected from the group consisting of alcohols containing one to six carbons, ketones containing one to six carbons, ethers containing one to six carbons, halide compounds, cyclanes and amides.

17. The high-density recordable optical disc of claim 16, wherein the alcohol containing one to six carbons is selected from the group consisting of methanol, ethanol, isopropanol, diacetonalchol (DAA), 2,2,3,3-tetrafluoropropanol, trichloroethanol, 2-chloroethanol, octafluoropentanol, or hexafluorobutanol.

18. The high-density recordable optical disc of claim 16, wherein the ketone is selected from the group consisting of acetone, methyl isobutyl ketone (MIBK), methyl ethyl ketone (MEK), and 3-hydroxy-3-methyl-2-butanone.

19. The high-density recordable optical disc of claim 16, wherein the halide compound is selected from the group consisting of chloroform, dichloromethane, and 1-chlorobutane.

20. The high-density recordable optical disc of claim 16, wherein the cyclane is methylcyclohexane (MCH).

21. The high-density recordable optical disc of claim 16, wherein the amide is selected from the group consisting of dimethylformamide (DMF) and dimethylacetamide (DMA).

22. The high-density recordable optical disc of claim 6, wherein the reflective layer is gold, silver, aluminum, silicon, copper, silver-titanium alloys, silver-chromium alloys, silver-copper alloys, and their combinations.

23. The high-density recordable optical disc of claim 6, wherein the combination of the first substrate and the second substrate is achieved using a method selected from spin coating, half-tone printing, hot gluing, and double-sided tapes.

24. The high-density recordable optical disc of claim 6, wherein the thickness of the reflective layer is between 50 nm and 200 nm.

25. The high-density recordable optical disc of claim 6, further comprising a plurality of recording layers and a plurality of reflective layers stacked together to form a multi-layer high-density recordable optical disc.

* * * * *